US008987309B2

(12) United States Patent  
Dorr et al.

(10) Patent No.: US 8,987,309 B2  
(45) Date of Patent: Mar. 24, 2015

(54) COMPOUNDS, PHARMACEUTICAL COMPOSITIONS AND METHODS OF USE OF 2-ARYL PYRIDYLAZOLES

(75) Inventors: Robert Dorr, Tucson, AZ (US); Gary Flynn, Oro Valley, AZ (US); Haiyong Han, Phoenix, AZ (US); Laurence Hurley, Tucson, AZ (US); Arthur Y. Shaw, Tucson, AZ (US)

(73) Assignees: The Translational Genomics Research Institute, Phoenix, AZ (US); The Arizona Board of Regents on behalf of the University of Arizona, Tucson, AZ (US)

( * ) Notice: Subject to any disclaimer, the term of this patent is extended or adjusted under 35 U.S.C. 154(b) by 242 days.

(21) Appl. No.: 13/264,967

(22) PCT Filed: Apr. 19, 2010

(86) PCT No.: PCT/US2010/031586  
§ 371 (c)(1),  
(2), (4) Date: Feb. 9, 2012

(87) PCT Pub. No.: WO2010/121243  
PCT Pub. Date: Oct. 21, 2010

(65) Prior Publication Data  
US 2012/0136029 A1 May 31, 2012

Related U.S. Application Data

(60) Provisional application No. 61/170,224, filed on Apr. 17, 2009.

(51) Int. Cl.  
A61K 31/443 (2006.01)  
C07D 413/04 (2006.01)  
C07D 213/81 (2006.01)  
A61K 31/42 (2006.01)  
A61K 45/06 (2006.01)  
C07D 263/32 (2006.01)  
C07D 413/10 (2006.01)  
C07D 413/14 (2006.01)

(52) U.S. Cl.  
CPC .............. *C07D 213/81* (2013.01); *A61K 31/42* (2013.01); *A61K 45/06* (2013.01); *C07D 263/32* (2013.01); *C07D 413/04* (2013.01); *C07D 413/10* (2013.01); *C07D 413/14* (2013.01)  
USPC ........................................ 514/340; 546/271.4

(58) Field of Classification Search  
USPC ........................................ 546/271.4; 514/340  
See application file for complete search history.

(56) References Cited

U.S. PATENT DOCUMENTS

2008/0015193 A1* 1/2008 Mendoza et al. .......... 514/236.8

OTHER PUBLICATIONS

Yu et al., "Physical characterization of, etc.," PSTT, vl. 1(3), 118-127 (1998).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Jain et al., "Polymorphism in Pharmacy", Indian Drugs, 1986, 23(6) 315-329.*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1995.*
Bernstein, "Polymorphism in . . . " p. 115-118, 272 (2002).*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*
LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders CO. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Golub et al, Science, vol. 286, Oct. 15, 1999, pp. 531-537.*
Ouaissi et al., "Rationale for Possible, etc.," Journal of Biomedicine and Biotechnology, 2011, Article: ID 315939, 1-8.*
EA Perez, Microtubule Inhibitors: Differentiating Tubulin-Inhibiting Agents Based on Mechanisms of Action, Clinical Activity, and Resistance, 8 Mol. Cancer Ther. 2086 (2009).
B. A. Teicher, Newer Cytotoxic Agents: Attacking Cancer Broadly, 14 Clin. Cancer Research 1610 (2008).
M. R. Harrison et al., Beyond Taxanes: A Review of Novel Agents that Target Mitotic Tubulin and Microtubules, Kinases, and Kinesins, 7 Clin. Adv. Hematology and Oncology 54 (2009).
A. L. Risinger et al., Microtubule Dynamics as a Target in Oncology 35 Cancer Treatment Reviews 265 (2009).
5. M. Schmidt & H. Bastians, Mitotic Drug Targets and the Development of Novel Anti-Mitotic Cancer Drugs, 10 Drug Resistance Updates 162 (2007).
6. W. N. Hait et al., Tubulin Targeting Agents, 2 Update on Cancer Therapeutics 1 (2007).

* cited by examiner

*Primary Examiner* — Patricia L Morris

(57) ABSTRACT

A 2-aryl-pyridylazole compound and derivatives useful in slowing the growth of cancer cells are disclosed. Also disclosed are methods of synthesizing the compound, methods of using pharmaceutical compositions containing the compound as an ingredient to slow the growth of cancer cells, and methods of treating cancer patients with pharmaceutical compositions containing the compound as an ingredient.

11 Claims, 16 Drawing Sheets

Fluorenone Series

Figure 3
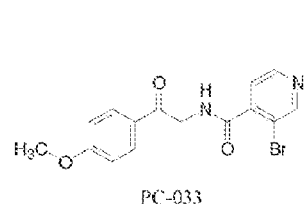
PC-033
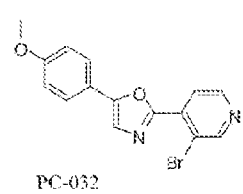
PC-032
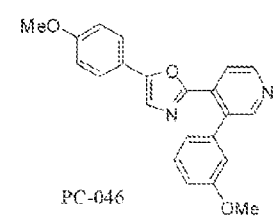
PC-046

Fig. 3. SAR exploration of UA-62784 (PC-001) fluorenone series.

Figure 5

Summary of PC analogs with selected Ar1 modifications

| Cmpd Code | R | Mol. Wt. | Clog P | BxPC3 DPC (-/-/-) IC50 [a] | BxPC3 DPC (-/+/+) IC50 | DPC-a Selectivity Index [b] | Dp85 IC50 [c] | CENT-E IC50 | MKLP-1 IC50 | KIF3C IC50 | MCAK IC50 |
|---|---|---|---|---|---|---|---|---|---|---|---|
| | | | | μM | | | | | μM | | |
| GA-62784 (PC-001) | | 353.37 | 5.44 | 0.023 | 0.012 | 1.9 | >100 | 7.3 | >100 | >100 | >100 |
| NS-44638 (PC-002) | | 323.34 | 5.43 | 5.3 | 2.8 | 1.89 | >100 | >100 | >100 | >100 | >100 |
| PC-004 | | 529.34 | 4.95 | 2.4 | 1.3 | 1.85 | >100 | >100 | 11.1 | >100 | >100 |
| PC-046 | | 368.13 | 3.23 | 0.013 | 0.0075 | 1.73 | >100 | >100 | >100 | >100 | >100 |
| PC-049 | | 328.12 | 3.4 | 20 | 18 | 1.11 | >100 | 11 | 14 | >100 | >100 |
| PC-053 | | 358.13 | 3.28 | 3.5 | 3.5 | 1.06 | >100 | >100 | >100 | >100 | >100 |
| PC-051 | | 412.36 | 4.93 | 15 | 12 | 1.25 | >100 | >100 | >100 | >100 | >100 |
| PC-050 | | 353.37 | 3.44 | >20 | >20 | 1 | >100 | >100 | >100 | >100 | >100 |
| PC-052 | | 346.25 | 3.56 | >20 | >20 | 1 | >100 | >100 | >100 | >100 | >100 |

Cmpd Code: compound code; [a] IC50 values were determined by 96 h MTT; [b] Ratio of IC50s of BxPC3 DPC (-/-/-) BxPC3 DPC (-/+/+); [c] IC50s of selected compounds against various kinesin targets. Clog P: logarithm of a compound's partition coefficient between n-octanol and water $P_{(C_{octanol}/C_{water})}$ (i.e., a measurement of a compound's hydrophobicity).

Figure 6

COMPOUNDS, PHARMACEUTICAL COMPOSITIONS AND METHODS OF USE OF 2-ARYL PYRIDYLAZOLES

CROSS REFERENCE TO RELATED APPLICATIONS

This application is the U.S. National Stage of PCT/US2010/031586 filed Apr. 19, 2010, which claims the benefit of U.S. Provisional Application No. 61/170,224 filed Apr. 17, 2009, the contents of each of which are herein incorporated by reference for all purposes.

BACKGROUND OF THE INVENTION

Generally, the invention pertains to the field of pharmaceutical compounds and more specifically to the field of 2-aryl pyridylazoles useful in the treatment of cancer.

Cancer is the second leading cause of death in the United States and despite new breakthroughs that have led to decreased mortality, many cancers remain refractory to treatment. Additionally, typical treatments such as chemotherapy, radiotherapy and surgery cause a broad spectrum of undesirable side effects. In addition, many cancers often develop resistance to current chemotherapies over time. Clearly the field is in significant need of novel compounds and methods of slowing the expansion of cancer cells and that are useful in the treatment of cancer.

SUMMARY OF THE INVENTION

The present invention provides among other things a pharmaceutical compound effective in the treatment of cancer.

It is an object of the invention to provide a pharmaceutical compound effective in the treatment of pancreatic cancer.

It is an object of the invention to provide a pharmaceutical compound effective in the treatment of ovarian cancer.

It is an object of the invention to provide a pharmaceutical compound effective in the treatment of lung cancer.

It is an object of the invention to provide a pharmaceutical compound effective in the treatment of prostate cancer.

It is an object of the invention to provide a pharmaceutical compound effective in the treatment of breast cancer.

It is an object of the invention to provide a pharmaceutical compound that slows the expansion of cancer cells.

The above and other objects may be achieved using a compound with the general structure:

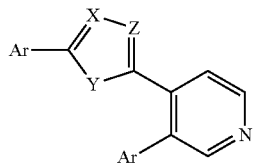

including all pharmaceutically acceptable salts thereof.

The groups denoted by X, Y, and Z may be independently CH, N, O, S, or NR. The group denoted R may be H or lower alkyl. The groups denoted Ar may be independently substituted aryl or heteroaryl groups of one of the following general structures:

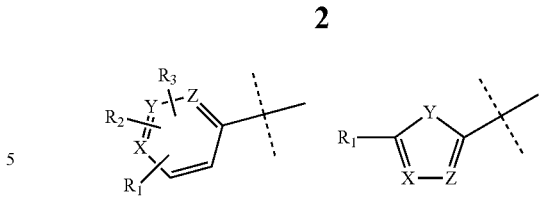

The groups denoted X, Y, and Z may be independently CH, N, O, S, or NR wherein R may be either H or alkyl. The groups denoted $R_1$, $R_2$, and $R_3$ may be independently H, alkyl, OH, OR', SH, $S(O)_nR'$, halogen, CN, $CO_2H$, $CO_2R'$, CONHR', $SO_2NHR'$, $CF_3$, $OCF_3$, or $O(CH_2)_nO$ wherein n is an integer and wherein R' may be . . . .

The above and other objects may be achieved by methods involving slowing the expansion of tumors with an effective amount of a pharmaceutical composition that includes the disclosed compound and, in some aspects of the invention, one or more pharmaceutically acceptable carriers.

The above and other objects may be achieved by methods involving treating a mammal with an effective amount of a pharmaceutical composition that includes the disclosed compound and, in some aspects of the invention, one or more pharmaceutically acceptable carriers.

Elements and acts in the figures are illustrated for simplicity and have not necessarily been rendered according to any particular sequence or embodiment.

BRIEF DESCRIPTION OF THE DRAWINGS

A more complete understanding of the present invention may be derived by referring to the detailed description when considered in connection with the following illustrative figure.

FIG. 3 depicts the structures of (D)PC-033, (D)PC-032, and (D)PC-046. The DPC designation and the PC designation are equivalent.

FIG. 5 depicts a summary of (D)PC analogs with selected Ar1 modifications.

FIG. 6 depicts a summary of (D)PC analogs with selected Ar2 modifications.

DETAILED DESCRIPTION OF THE INVENTION

Figure 1:
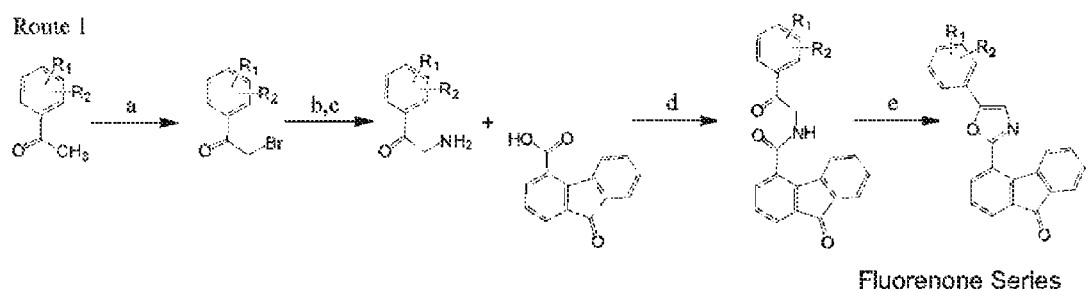
FIG. 1 depicts a synthetic approach to diaryl oxazoles (fluroenone series.)

Herein the Inventors disclose a compound with a formula of:

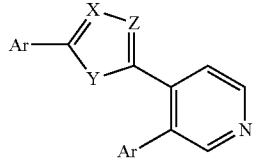

The groups denoted X, Y, and Z may be independently CH, N, O, S, or NR. The group denoted R may be H or lower alkyl. The groups denoted Ar are independently substituted aryl or heteroaryl groups of one of the following general structures:

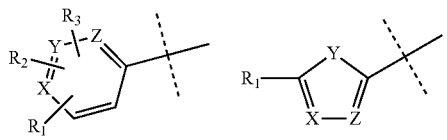

The groups denoted X, Y, and Z may be independently CH, N, O, S, or NR wherein R may be either H or alkyl. The groups denoted $R_1$, $R_2$, and $R_3$ may be independently H, alkyl, OH, OR', SH, $S(O)_n R'$, halogen, CN, $CO_2H$, $CO_2R'$, CONHR', $SO_2NHR'$, $CF_3$, $OCF_3$, or $O(CH_2)_n O$ wherein n is an integer and wherein R' may be H or alkyl.

A —$C_1$-$C_6$ alkyl group, also known as a lower alkyl, includes any straight or branched, saturated or unsaturated, substituted or unsubstituted hydrocarbon comprised of between one and six carbon atoms. Examples of —$C_1$-$C_6$ alkyl groups include, but are not limited to methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —$C_1$-$C_6$ alkyl groups may include any applicable chemical moieties. Examples of groups that may be substituted onto any of the above listed —$C_1$-$C_6$ alkyl groups include but are not limited to the following examples: halo, —$C_1$-$C_6$ alkyl, —O—($C_1$-$C_6$ alkyl), —OH, —CN, —COOR', —OC(O)R', —NHR', N(R')$_2$, —NHC(O)R' or —C(O)NHR' groups. The groups denoted R' above may be —H or any —$C_1$-$C_6$ alkyl.

An aryl group includes any unsubstituted or substituted phenyl or napthyl group. Examples of groups that may be substituted onto ay aryl group include, but are not limited to: halo, —$C_1$-$C_6$ alkyl, —O—($C_1$-$C_6$ alkyl), —OH, —CN, —COOR', —OC(O)R', NHR', N(R') 2, —NHC(O), R', or —C(O)NEtR'. The group denoted R' may be —H or any —$C_1$-$C_6$ alkyl.

The disclosed compound and its intermediates may exist in different tautomeric forms. Tautomers include any structural isomers of different energies that have a low energy barrier to interconversion. One example is proton tautomers (prototropic tautomers.) In this example, the interconversions occur via the migration of a proton. Examples of prototropic tautomers include but are not limited to keto-enol and imine-enamine isomerizations. In another example illustrated graphically below, proton migration between the 1-position and 3-position nitrogen atoms of the benzimidazole ring may occur. As a result, Formulas Ia and Ib are tautomeric forms of each other:

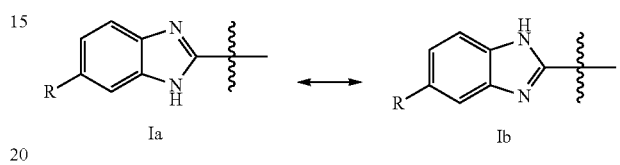

The invention further encompasses any other physiochemical or sterochemical form that the disclosed compound may assume. Such forms include diastereomers, racemates, isolated enantiomers, hydrated forms, solvated forms, or any other known or yet to be disclosed crystalline, polymorphic crystalline, or amorphous form. Amorphous forms lack a distinguishable crystal lattice and therefore lack an orderly arrangement of structural units. Many pharmaceutical compounds have amorphous forms. Methods of generating such chemical forms will be well known by one with skill in the art.

In some aspects of the invention the disclosed compound is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl)phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated by one skilled in the art that such pharmaceutically acceptable salts may be used in the formulation of a pharmacological composition. Such salts may be prepared by reacting the disclosed compound with a suitable acid in a manner known by those skilled in the art.

The invention further encompasses aspects in which a protecting group is added to the compound. One skilled in the art would recognize that during the synthesis of complex molecules, one group on the disclosed compound may happen to interfere with an intended reaction that includes a second group on the compound. Temporarily masking or protecting the first group encourages the desired reaction. Protection involves introducing a protecting group to a group to be protected, carrying out the desired reaction, and removing the protecting group Removal of the protecting group may be referred to as deprotection. Examples of compounds to be protected in some syntheses include hydroxy groups, amine groups, carbonyl groups, carboxyl groups and thiols.

Many protective groups and reagents capable of introducing them into synthetic processes have been and are continuing to be developed today. A protecting group may result from any chemical synthesis that selectively attaches a group that is resistant to certain reagents to the chemical group to be protected without significant effects on any other chemical groups in the molecule, remains stable throughout the synthesis, and may be removed through conditions that do not adversely react with the protected group, nor any other chemical group in the molecule. Multiple protecting groups may be added throughout a synthesis and one skilled in the art would be able to develop a strategy for specific addition and removal of the protecting groups to and from the groups to be protected.

Protecting groups, reagents that add those groups, preparations of those reagents, protection and deprotection strategies under a variety of conditions, including complex syntheses with mutually complementary protecting groups are all well known in the art. Nonlimiting examples of all of these may be found in Green et al, *Protective Groups in Organic Chemistry* 2$^{nd}$ Ed., (Wiley 1991), and Harrison et al, *Compendium of Synthetic Organic Methods*, Vols. 1-8 (Wiley, 1971-1996) both of which hereby incorporated by reference in their entireties.

Racemates, individual enantiomers, or diasteromers of the disclosed compound may be prepared by specific synthesis or resolution through any method now known or yet to be disclosed. For example, the disclosed compound may be resolved into it enantiomers by the formation of diastereomeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

Different aspects of the invention may be prepared via the general synthetic procedures outlined below. It will be readily apparent to one skilled in the art know how to prepare aspects of the invention using the correct starting materials, synthetic intermediates and reagents from the exemplary procedures below.

$^1$H and $^{13}$C NMR spectra were measured at 300 MHz on a Bruker 300-MHz NMR spectrometer. Chemical shifts were reported relative to internal CDCl3 (1H, 7.26 ppm and 13C, 77.0 ppm) and CD3OD (1H, 3.30 ppm and 13C, 49.2 ppm). Flash column chromatography was performed on silica gel 60 (35-75 m) and thin layer chromatography on silica gel 60 F254 aluminum sheets. Melting points were determined on an electrothermal melting apparatus. High-resolution mass spectrometry spectra were recorded using electrospray ionization or matrix-assisted laser desorption ionization/time of flight techniques.

One method of synthesizing the disclosed compound is shown in FIG. 1. Referring now to FIG. 1, the conditions denoted by a include treatment with NBS, TMS-OTf or any equivalents. The conditions denoted by b include treatment with NaN3, DMSO and any equivalents that may be treated 30 minutes or more at ambient temperature. The conditions denoted by c include treatment with PPh$_3$, TsOH, THF, or any equivalents that may be incubated at least 24 hours. The conditions denoted by d include treatment with EDC, DIEA, DCM or any equivalents. The conditions denoted by e includes POCl$_3$ diluted in an excess of DMF. The ratio of DMF to POCl3 may be about 5:1 and the mixture incubated about 2 hours at about 80° C.

Figure 2:
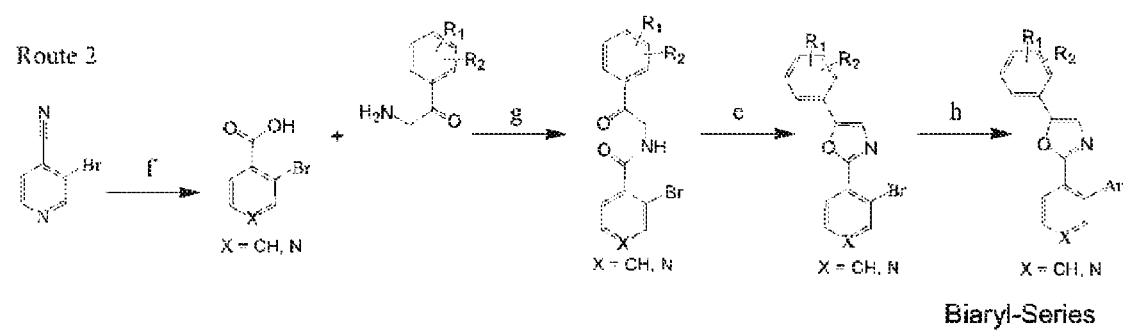
FIG. 2 depicts a synthetic approach to diaryl oxazoles (biaryl-series.)

Another method of synthesizing the disclosed compound shown in FIG. 2. Referring now to FIG. 2, the conditions denoted by f include treatment with Ar—B(OH)$_2$, Pd(PPh$_3$)$_4$, Na$_2$CO$_3$, and water in an excess of DME. The group denoted Ar may be independently substituted aryl or heteroaryl groups of one of the following general structures:

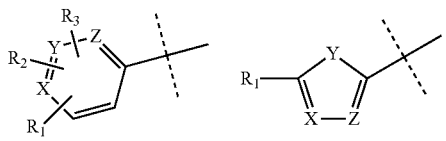

With the groups denoted X, Y, and Z may be independently CH, N, O, S, or NR wherein R may be either H or alkyl. The groups denoted R$_1$, R$_2$, and R$_3$ may be independently H, alkyl, OH, OR', SH, S(O)$_n$R', halogen, CN, CO$_2$H, CO$_2$R', CONHR', SO$_2$NHR', CF$_3$, OCF$_3$, or O(CH$_2$)$_n$O wherein n is an integer and wherein R' may be either H or alkyl The ratio of DME to water may be about 3:1. The mixture may be refluxed at least two hours. The conditions denoted by g and h include conditions known in the art to bring about the disclosed result.

The 2-bromoacetophenone and 2-aminoacetophenone intermediates may be prepared by bromination of commercial acetophenone precursors with N-bromosuccinamide (Guha et al., 2005) and, as required, subsequent displacement of the resulting 2-bromoacetophenone with sodium azide and phosphene reduction to provide the corresponding 2-aminoacetophenone tosylate salt (Holub et al., 2004). Direct coupling of the appropriate 2-aminoacetophenone salts to commercially available carboxylic acids followed by a Robinson-Gabriel cyclodehydration of the resulting keto-amide with phosphorous oxy-chloride (Nicolaou et al., 2004) was used to prepare many aspects of the disclosed compound using route 1 (FIG. 2). Under route 2 above, palladium catalyzed coupling of commercially available aryl boronic acids to a common 2-(2-bromoaryl)oxazole intermediate was used to efficiently prepare a large series of 2-biaryl-oxazole analogs (Meanwell et al., 1993).

The invention further encompasses pharmaceutical compositions that include the disclosed compound as an ingredient. Such pharmaceutical compositions may take any physical form necessary depending on a number of factors including the desired method of administration and the physicochemical and stereochemical form taken by the disclosed compound or pharmaceutically acceptable salts of the compound. Such physical forms include a solid, liquid, gas, sol, gel, aerosol, or any other physical form now known or yet to be disclosed. The concept of a pharmaceutical composition including the disclosed compound also encompasses the disclosed compound or a pharmaceutically acceptable salt thereof without any other additive. The physical form of the invention may affect the route of administration and one skilled in the art would know to choose a route of administration that takes into consideration both the physical form of the compound and the disorder to be treated. Pharmaceutical compositions that include the disclosed compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the disclosed compound with regard to one or more biochemical pathways.

Pharmaceutical compositions including the disclosed compound include materials capable of modifying the physical form of a dosage unit. In one nonlimiting example, the composition includes a material that forms a coating that holds in the compound. Materials that may be used in such a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include the disclosed compound may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable or synthetic oils,) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the disclosed compound may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the disclosed compound may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Cancer cells include any cells derived from a tumor, neoplasm, malignancy, metastasis, lesion, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Exapansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include caspase dependent and independent pathways, autophagy, necrosis, apoptosis, and mitochondrial dependent and independent processes and further include any such processes yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells,) endothelial cells that may differentiate into blood vessel structures in the process of angiogenesis or vasculogenesis, or fibroblasts in proximity to the cancer cells.

Determination of an effective amount of the disclosed compound is within the capability of those skilled in the art, especially in light of the detailed disclosure provided herein. The effective amount of a pharmaceutical composition used to effect a particular purpose as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a pharmaceutical composition may be determined by standard pharmaceutical procedures in cell cultures or animals. Examples include the determination of the $IC_{50}$ (the half maximal inhibitory concentration) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of the disclosed compound to results in the slowing of expansion of the cancer cells would preferably result in a concentration at or near the target tissue that is effective in slowing cellular exapansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the disclosed compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including the disclosed compound may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-79). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype). Further examples include leukoplakia, in which a benign-appearing hyperplastic or dysplastic lesion of the epithelium, or Bowen's disease, a carcinoma in situ, are pre-neoplastic lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the disclosed compound may be determined by one or more physical factors such as tumor size or tumor grade. In other aspects of the invention, use of the disclosed compound may be determined by the heightened, reduced, or normal expression of one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality.

Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the disclosed compound is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination with the disclosed compound may include nucleic acid binding compositions such as cis-diamminedichloro platinum (II) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that may be used in combination with the pharmaceutical composition including the disclosed compound are hematopoietic colony stimulating factors. Examples of hematopoietic colony stimulating factors include, but are not limited to, filgrastim, sargramostim, molgramostim and epoietin alfa. Alternatively, the pharmaceutical composition including the disclosed compound may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the disclosed compound may include analgesic agents. Such agents may be opioid or non-opioid analgesic. Non-limiting examples of opioid analgesics inlcude morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions including the disclosed compound may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the disclosed compound may then be administered to the patient prior to restoring the entity's bone marrow by addition of either the patient's own or donor stem cells.

Cancers that may be treated by pharmaceutical compositions including the disclosed compound either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendo-theliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Examples that represent different aspects of the invention follow. Such examples should not be construed as limiting the scope of the disclosure. Alternative mechanistic pathways and analogous structures within the scope of the invention would be apparent to those skilled in the art.

EXAMPLE

Chemistry. $^1$H and $^{13}$C NMR spectra were measured at 300 MHz on a Bruker 300-MHz NMR spectrometer. Chemical shifts were reported relative to internal CDCl3 (1H, 7.26 ppm; 13C, 77.0 ppm) and CD3OD (1H, 3.30 ppm; 13C, 49.2 ppm). Flash-column chromatography was performed on Silica Gel 60 (35-75 µm), and thin-layer chromatography was performed on Silica Gel 60 F254 aluminum sheets. Melting points were determined on an electrothermal melting apparatus. High-resolution mass spectrometry spectra were recorded using electrospray ionization or matrix-assisted laser desorption ionization/time-of-flight techniques at the University of Arizona Mass Spectrometry Core Facility (Chemistry Department, Tucson, Ariz.).

Chemicals. The two synthetic approaches used to prepare 2,5-diaryl oxazole compounds are outlined in FIG. 1. The 2-bromoacetophenone and 2-aminoacetophenone intermediates were either available from commercial sources or prepared by bromination of commercial acetophenone precursors with N-bromosuccinamide (Guha et al., 2006) and, as required, subsequent displacement of the resulting 2-bromoacetophenone with sodium azide and phosphene reduction to provide the corresponding 2-aminoacetophenone tosylate salt (Holub et al., 2004). Direct coupling of the appropriate 2-aminoacetophenone salts to commercially available carboxylic acids followed by a Robinson-Gabriel cyclodehydration of the resulting ketoamide with phosphorous oxychloride (Nicolaou et al., 2004) was used to prepare many initial UA-62784 analogs (FIG. 1). In a second more flexible approach (FIG. 2), palladium catalyzed coupling of commercially available aryl boronic acids to a common 2-(2-bromoaryl)oxazole intermediate was used to efficiently prepare a large series of 2-biaryl-oxazole analogs (Meanwell et al., 1993). Preparation of DPC-033, DPC-032, and DPC-046 as described below illustrates this general procedure (FIG. 2). A mixture of 2-amino-4-methoxyacetophenone hydrochloride (5.0 g, 22.32 mmol; Sigma-Aldrich, St. Louis, Mo.), 3-bromo-4-pyridinecarboxylic acid (4.96 g, 24.55 mmol; Matrix Scientific, Columbia, S.C.), EDC (5.12 g, 26.8 mmol), and DIEA (7.77 ml, 44.6 mmol) was dissolved in DCM (120 ml). The reaction mixture was stirred at 22° C. for 18 h. The mixture was washed with 1 N NaOH, 0.2 N HCl, and brine. The organic layer was dried over MgSO4, evaporated in vacuo, and then purified by column chromatography on silica gel (DCM/ethyl acetate 3/1) to obtain PC-033 (3.25 g, 9.31 mmol, 41.7% yield). 1H NMR (300 MHz, CDCl3) 3.89 (s, 3H), 7.06 (d, J 9.0 Hz, 2H), 7.58 (d, J 4.8 Hz, 1H), 8.05 (d, J 9.0 Hz, 2H), 8.62 (d, J 4.8 Hz, 1H), 8.79 (s, 1H) ppm. A mixture of PC-033 (3.25 g, 9.31 mmol) and phosphorus oxychloride (1.784 ml, 18.62 mmol) in DMF (10 ml) was stirred at 80° C. for 2 h. The reaction solution was cooled to 22° C. and diluted with ethyl acetate (10 ml) and washed with water twice at 10 ml. The organic layer was dried over MgSO4, evaporated in vacuo, and purified by column chromatography on silica gel (DCM/ethyl acetate 3/1) to obtain DPC-032 (2.7 g, 8.15 mmol, 88% yield). 1H NMR (300 MHz, CDCl3), 3.71 (s, 3 H), 6.86 (d, J 9.0 Hz, 2 H), 7.46 (s, 1 H), 7.58 (d, J 9.0 Hz, 2H), 8.22 (d, J 6.0 Hz, 1H), 8.55 (d, J 6.0 Hz, 1H), 8.87 (s, 1H) ppm. 13C NMR (75 MHz, CDCl3) 55.38, 114.81, 116.84, 118.53, 124.07, 125.11, 126.84, 140.03, 141.09, 148.03, 154.39, 155.76, 161.32 ppm. High-resolution mass spectrometry (M H) calculated for C15H12BrN2O2 331.0082; found 331.0070. DPC-032 (0.15 g, 0.453 mmol), 3-methoxyphenylboronic acid (0.138 g, 0.906 mmol), tetrakis(triphenylphosphine)palladium (0.026 g, 0.023 mmol), and sodium carbonate (0.144 g, 1.359 mmol) were stirred in DME/H2O (9 ml/3 ml) under argon atmosphere at reflux for 2 h. The reaction mixture was diluted with ethyl acetate (10 ml) and washed with water and brine. The organic layer was dried over MgSO4 and evaporated in vacuo to obtain the crude product. Further purification by gradient silica gel chromatography (hexane/ethyl acetate 3/1 to 1/2) afforded PC-046 (0.143 g, 0.399 mmol, 88% yield). 1H NMR (300 MHz, CDCl3) 3.81 (s, 3H), 3.84 (s, 3H), 6.83 (d, J 2.1 Hz, 1H), 6.87 (d, J 2.7 Hz, 1H), 6.95-6.97 (m, 2H), 7.03 (dd, J 2.7, 1.5 Hz, 1H), 7.15 (dd, J 6.9, 2.1 Hz, 2H), 7.29 (d, J 6.9 Hz, 1H), 7.39 (t, J 7.8 Hz, 1H), 8.04 (d, J 5.1 Hz, 1H), 8.69 (s, 1H), 8.73 (d, J 5.1 Hz, 1H) ppm. 13C NMR (75 MHz, CDCl3) 55.75, 55.78, 113.98, 114.67, 115.14, 120.48, 122.11, 122.26, 126.18, 129.77, 133.07, 135.23, 139.97, 149.32, 152.21, 152.88, 158.61, 159.94, 160.49 ppm. HRMS (M H) calculated for C22H18N2O3 359.1396; found 359.1392.

Cell lines and Culture Conditions. Human pancreatic cancer cell lines MiaPaCa-2 (Yunis et al., 1977), Panc-1 (Lieber et al., 1975), and BxPC3 (Tan et al., 1986) were purchased from the American Type Culture Collection (Manassas, Va.) and cultured in a humidified incubator at 37° C., 5% CO2, in RPMI 1640 medium (CellGro, Manassas, Va.) supplemented with 10% heat-inactivated bovine calf serum, 2 mM L-glutamine, 100 U/ml penicillin, and 100 g/ml streptomycin (Invitrogen, Carlsbad, Calif.). MiaPaCa-2 (CRL-1420) is an adherent epithelial human pancreatic cancer cell line with a doubling time of approximately 40 h (Yunis et al., 1977). Panc-1 (CRL-1469) is an undifferentiated human pancreatic epithelial cell line with a doubling time of approximately 52 h (Lieber et al., 1975). The BxPC3 cell line DPC-4(−/−) and its isogenic restored wild-type DPC-4(+/+) cell line were developed and cultured as described previously (Wang et al., 2006). In brief, a DPC-4-expressing construct (pMSCV-neoDPC-4) was created by amplifying full-length cDNA of DPC-4 using reverse transcriptase-PCR and subcloning into the multiple cloning site of a retroviral vector (pMSCVneo). The DPC-4-expressing construct was cotransfected into the BxPC3 DPC-4(−/−) cells using a packaging cell line, resulting in a cell line that constitutively expresses DPC-4. The expression of DPC-4 was confirmed by Western blotting (Wang et al., 2006).

Verification of Cell Line Identities. Cell line identities were verified by STR profiling (Collins et al., 2004) by the Human Origins Genotyping Laboratory at the University of Arizona, using the Amp-FISTR Identifier PCR amplification kit (Applied Biosystems, Foster City, Calif.). This method simultaneously amplifies 15 STR loci and amelogenin in a single tube, using five dyes, 6-carboxyfluorescein, 2,7-dimethyloxy 45-dichloro 6-carboxyfluorescein, NED, PET, and LIZ, which are then separated on a 3730 Genetic Analyzer (Applied Biosystems). GeneMarker, version 1.7, software was used for analysis (Soft Genetics, State College, Pa.). AmpFISTR control DNA and the AmpFISTR allelic ladder were run concurrently. Results were compared to published STR sequences from the American Type Culture Collection.

Cytotoxicity Assays. Cytotoxicity assays in the mechanism of action studies were performed according to Mosmann (1983), wherein the activity of mitochondrial reductases were measured using 3-(4,5-dimethylthiozol-3-yl)-2,5-diphenyltetrozolium bromide dye. In brief, cells were seeded in 96-well plates and incubated for various times at 37° C. Inhibition of cell growth was measured by adding 3-(4,5-dimethylthiozol-3-yl)-2,5-diphenyltetrozolium bromide dye, and after an additional 4 h of incubation at 37° C., the 96-well plates were centrifuged, and the culture supernatant was removed. DMSO was added to each well to solubilize the formazan crystals, and the optical density was read at 540 nm on a Quant Spectrophotometer (BioTek Instruments, Winooski, Vt.). Cell growth inhibition data are expressed as percentage of survival compared with untreated cells. The $IC_{50}$ is defined as the drug concentration required to produce 50% growth inhibition. Results are mean S.E.M. (n 3).

Preparation of DPC-046. For in vitro studies, a 50 mM stock solution of DPC-046 (also known interchangeably as PC-046) was prepared in DMSO and subsequently diluted into cell culture medium at working concentrations, ensuring that the final DMSO concentration used in cell culture is less than 0.1%, which we have previously determined to have no cytotoxic effect on our cell lines. For in vivo studies, DPC-046 was prepared in 88% DMSO, 10% Tween 80, and 2% benzyl alcohol.

Kinesin ATPase Assay. The colorimetric kinesin ATPase assay was purchased from Cytoskeleton, Inc. (Denver, Colo.) and performed as indicated by the manufacturer (Funk et al., 2004). In short, 0.2 to 1.0 g of purified recombinant CENP-E (Yen et al., 1991; Lombillo et al., 1995), Eg5/kinesin spindle protein (Sawin et al., 1992), MCAK (Hunter et al., 2003), and MLKP-1 (Nislow et al., 1992) mitotic kinesin motor proteins and the nonmitotic KIF3C kinesin (Yang and Goldstein, 1998) were added to paclitaxel-stabilized microtubules in a 96-well plate. Increasing amounts of UA-62784 or PC analogs were added to the wells before the addition of ATP (Sigma-Aldrich), and the reaction was incubated at 22° C. for 5 min. The CytoPhos reagent (Cytoskeleton Inc.,) was added to halt the reaction, and color was allowed to develop for 10 min. Absorbance at 650 nm was measured in a Quant Spectrophotometer (BioTek Instruments).

Measurement of Cell Cycle. The percentage of cells in different cell cycle phases of division was measured by flow cytometry (Darzynkiewicz et al., 1996) using propidium iodide (PI) (Sigma-Aldrich). In brief, cells were treated with PC-046 for 24 to 72 h, fixed with 70% ethanol overnight, and then stained with 40 g/ml PI and 0.5 mg/ml RNase A for 30 min at 37° C. PI fluorescence was measured on a FACScan (BD Biosciences, San Jose, Calif.) and analyzed using ModFit (Verify Software, Topsham, Me.). Data are mean S.E.M. (n 3).

Measurement of Apoptosis and Necrosis. Apoptosis and necrosis after DPC-046 treatment was measured at 24 to 72 h by flow cytometry (Vermes et al., 1995) using Annexin V-Alexa Fluor 488 (Invitrogen) and propidium iodide (BioVision, Mountain View, Calif.). Because of the greater photostability of Alexa Fluor 488 over fluorescein isothiocyanate, we substituted Alexa Fluor 488-labeled Annexin V for fluorescein isothiocyanate-labeled Annexin V. Apoptosis was measured by positive Annexin V staining, indicating the translocation of phosphatidylserine on the cell membrane of apoptotic cells, whereas necrosis was measured by dual labeling of Annexin V and propidium iodide of necrotic cells. Unstained cells were deemed alive. Fluorescence of Annexin V-Alexa Fluor 488 and PI was measured on FL1 and FL2, respectively, on a BD Biosciences FACScan using CellQuest Pro software (BD Biosciences). Data are mean S.E.M. (n 3).

Measurement of Macromolecular Synthesis. Radiolabeled precursors of DNA ([$^3$H]thymidine) and protein ([$^{14}$C]valine) were obtained from GE Healthcare (Piscataway, N.J.). The RNA precursor [$^3$H]uridine was obtained from MP Biomedical (Irvine, Calif.). In brief, cells were plated in 96-well plates and allowed to adhere before adding DPC-046 for 24 to 72 h. Radiolabeled precursors (1 Ci/well for thymidine and uridine, and 0.05 Ci/well for valine) were added and allowed to incorporate for 6 h at 37° C. Cells were harvested onto Unifilter-96 GF/B filterplates using a Packard Filtermate 96-well harvester and counted using a Packard Top Count NXT 96-well scintillation counter (PerkinElmer Life and Analytical Sciences, Boston, Mass.).

In Vivo Studies. Six- to 7-week-old male SCID mice were implanted with $10 \times 10^6$ MiaPaCa-2 cells in MatriGel (BD Biosciences) subcutaneously in the flank to establish tumors. Once the tumors reached approximately 100 $mm^3$ and were palpable (approximately 3 weeks later), DPC-046 treatment was initiated. DPC-046 was prepared in 88% DMSO, 10% Tween 80, and 2% benzyl alcohol. Mice were administered vehicle alone or 44, 55, or 66 mg/kg/day DPC-046 intraperitoneally for 5 consecutive days. Tumor size, body weight, and general health of each mouse were recorded every 3rd day for the duration of the study.

Kinase Screening. Initial kinase screening was performed by Amphora Discovery Corporation (Durham, N.C.). Forty-eight protein kinases were screened using a 10 μM concentration of 12 DPC compounds or UA-62784 by measuring [$^{33}$P]ATP incorporation into a specific kinase substrate. Subsequent kinase screening and $IC_{50}$ determination were performed by SignalChem Pharmaceuticals, Inc. (Richmond, BC, Canada) using a 25 μM concentration of DPC-046 (for the screening) and eight concentrations of DPC-046 from 10 nM to 50 μM for the dose-response curve.

Pharmacokinetic Studies. The pharmacokinetics of DPC-046 in nontumor bearing SCID mice was determined after intravenous administration of a single dose of 88 mg/kg. Plasma samples were collected at 0, 1, 5, 15, 30, 60, 90, 120, 240, 480, 960, and 1440 min after dosing. Plasma DPC-046 concentrations were analyzed by reversed-phase chromatography and tandem mass spectrometry. In brief, mouse plasma was mixed with 99 volumes of acetonitrile, and an aliquot of the supernatant was injected onto the LC-MS. The LC-MS analysis was performed on a ThermoFinnigan Quantum Ultra triple quadrupole mass spectrometer (Thermo Fisher Scientific, Waltham, Mass.) in tandem with a Surveyor LC system. Chromatographic separation was achieved with a Luna C18 column (2×50 mm, 50 (Phenomenex, Torrance, Calif.) and a mobile phase of 47.5% acetonitrile with 5 mM ammonium formate and 0.05% trifluoroacetic acid at a flow rate of 0.3 ml/min. Analytes were ionized by positive electrospray ionization and detected using selective reaction monitoring for transitions of 395/182 at a collision energy of 52 eV and 395/197 at a collision energy of 39 eV. The assay is linear over the range of 0.05 to 5 μg/ml from 10 μl of mouse plasma. The DPC-046 concentration-time data [half-life, area under curve (AUC) of the plasma concentration-time profile, systemic clearance, and volume of distribution] were analyzed by the noncompartmental approach using WinNonlin, version 5.2 (Pharsight, Mountain View, Calif.). Data are mean±S.E.M. (n=3).

Plasma Protein Binding. Plasma protein binding of DPC-046 was determined in human and mouse plasma using rapid equilibrium dialysis (RED) devices manufactured by Thermo Fisher Scientific. Plasma pH was adjusted to 7.4 and spiked with DPC-046 to a final plasma concentration of 1 μg/ml. Aliquots (500 μl) of the spiked plasma were placed into the sample chamber, and 750 μl of phosphate-buffered saline were placed into the adjacent chamber. Triplicate samples were loaded into the RED devices. The RED devices were incubated at 37° C. on an orbital shaker operating at 100 rpm for 24 h. Preliminary studies were conducted to show that equilibrium is reached at 24 h and to confirm drug stability at 37° C. for 24 h. After the incubation, aliquots of plasma and buffer were removed for the analysis of DPC-046 concentration by LC-MS-MS as described above.

Development of SAR for UA-62784 and Biaryl Analogs. Because of its high potency against isogenic BxPC3 cell lines, UA-62784 was used as the starting point for the chemical synthesis campaign. The limitations of UA-62784 include a lack of solubility that relates to its high calculated partition coefficient (Clog P 5.44) and a relatively low (2-fold) selectivity index for BxPC3 DPC-4(−/−) cells. In addition to addressing these limitations, the analog studies were directed toward understanding the essential pharmacophore elements and the biological targets responsible for the growth-inhibitory effects. Keeping the oxazole core of UA-62784 constant, the two aryl substituents (Ar1 and Ar2) were systematically optimized for the fluorenone series (FIG. 5). Summary data for Ar1 SAR are listed in FIG. 6, and SAR data for Ar2 are listed in FIG. 7.

Figure 4:
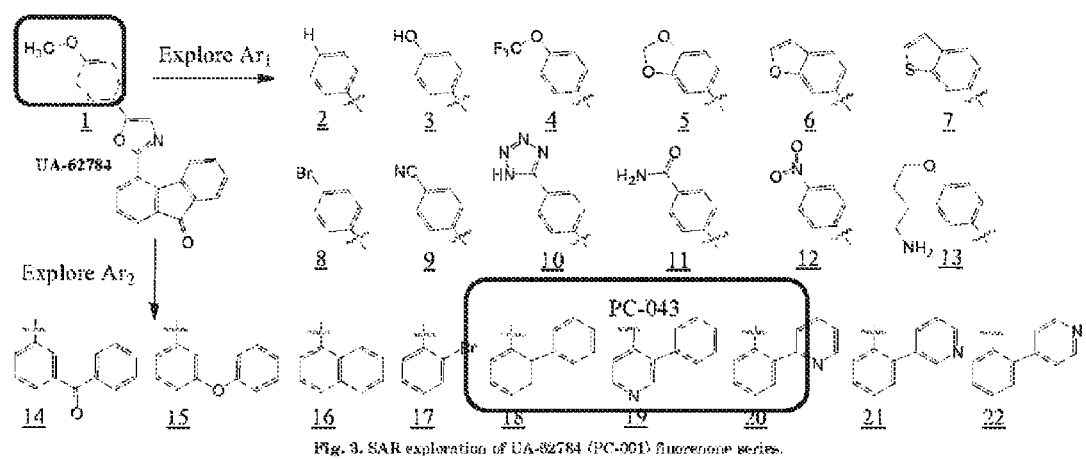
FIG. 4 depicts SAR exploration of the UA-62784 (D)PC-001 fluorenone series.

It is a striking revelation that high potency against BxPC3 cell lines is only seen where Ar1 is 4-methoxy-phenyl (compounds DPC-001 and PC-046). Even minor modifications, such as replacement of the 4-methoxy group with 4-hydroxy or 4 trifluoromethoxy at Ar1, are not well tolerated. These tight SAR observations suggest a specific target or a closely related class of targets as responsible for the observed cytotoxic activity. Therefore, Ar1 was held as 4-methoxyphenyl, and the influence of the fluorenone Ar2 system was systematically explored (Table 2). The key pharmacophore elements for Ar2 were also quite specific with the 2-biaryl analog DPC-026 (Table 2), the first variant that retained high potency. Subsequent biaryl analogs (DPC-038, DPC-039, DPC-043, and DPC-045) incorporated a pyridine ring in hopes of improving solubility (Table 2). Of these compounds, DPC-043 and DPC-045 retained potency. For ease of synthesis reasons, DPC-043 was selected for further modification (FIG. 4). Three pyridylphenyl analogs were found to be potent in the low nanomolar range, with DPC-046 being the most potent (Table 2). The selectivity index for different analogs was based on the ratio of the $IC_{50}$ in BxPC3 DPC-4 (+/+) to BxPC3 DPC-4(−/−) cells and ranged from 0.12 to 1.9 in this analog series. Indeed, all but one of the selectivity scores in this series are lower than the 1.9 for parent compound UA-62784 (Table 1, compound DPC-001).

Kinesin ATPase Inhibition. Five different purified recombinant kinesin motor proteins were evaluated for inhibition by selected PC analogs. This included four mitotic kinesins, Eg5, CENP-E, MKLP-1, and MCAK, and the nonmitotic (neuronal) kinesin KIF3C (Hirokawa and Noda, 2008). These were characterized for ATPase inhibitory activity with the DPC series. None of the 23 analogs selected for kinesin testing was inhibitory for the mitotic kinesin Eg5 or the neuronal kinesin KIF3C at concentrations up to 100 µM (Tables 1 and 2). This upper concentration limit was always far greater than the cytotoxic $IC_{50}$s for each analog. It is interesting that only two analogs inhibited CENP-E; the $IC_{50}$ for DPC-042 (Table 2) was 55 µM, and the $IC_{50}$ for PC-053 (Table 1) was 11 µM. Although the position of the methoxy substituents at Ar1 is different in both analogs, a 2-aryl-4-pyridryl moiety at Ar2 is a common feature. Likewise, only one analog, DPC-024, inhibited MCAK, with an $IC_{50}$ of 39 µM (Table 2). The structure of DPC-024 differs from the others by substitution of the 2-aryl-4-pyridryl moiety at Ar2, with a simple 4-phenoxyphenyl group. Analog DPC-024 had the lowest overall cytotoxic potency for the 25 compounds tested for kinesin inhibition of the 23 analogs tested, with an $IC_{50}$=43 µM. In contrast, growth inhibitory potency in the BxPC3 cell line showed significant correlations with CENP-E and MKLP-1, albeit with low $r^2$ values. For CENP-E, the $r^2$ was 0.27 (p=0.049) and, for MKLP-1, the $r^2$ value was 0.23 (p=0.038). Overall, there were little data to suggest that mitotic kinesins comprise the molecular targets of this group of compounds.

Protein Kinase Inhibition. Protein kinases play critical roles in all aspects of cellular metabolism: survival, proliferation, signaling, division, repair, and metastasis and are frequently activated in cancer. Thus, a compound that targets kinases can be a valuable tool in the oncologist's arsenal of treatment options. Because DPC-046 demonstrated the greatest cytotoxicity against both DPC-4(+/+) and DPC-4(−/−) BxPC3 cells, this compound was further characterized for its kinase inhibitory activity. This analog retains the 4-methoxyphenyl side group at Ar1 and the oxazole core of UA-62784 but substitutes a 2-(m-methoxypheny)-4-pyridyl moiety for the fluorenone functionality at Ar2. The initial screen of 48 protein kinases incubated with 12 compounds (10 µM each) and UA-62784 showed 50% inhibition of CDK2/cyclin A for compounds DPC-001 (57% inhibition), DPC-002 (57% inhibition), and PC-004 (57% inhibition). There was no significant (>50%) inhibition of any protein kinases by compounds DPC-024, DPC-027, DPC-102, DPC-103, and UA-62784. Analog DPC-026 inhibited PDGFRα (59% inhibition) and PDGFRβ (43% inhibition). The only compounds showing substantial multikinase inhibition were DPC-043 and DPC-046. Analog DPC-043 produced nearly 50% inhibition of PIM-1 kinase and TrkB kinase, whereas DPC-046 inhibited PIM-1 (50%), PDGFRα (46%), and TrkB (55%). Based on these initial results, a follow-up screen was performed using 25 µM DPC-046, the standard drug concentration used by SignalChem Pharmaceuticals, Inc., for kinase inhibition assays. DPC-046 inhibited three kinases by more than 70%: IRAK-4, PIM-1, and TrkB (FIG. 5). The $IC_{50}$ of these three kinases were measured using an eight-point concentration range from 10 nM to 50 µM. The $IC_{50}$ values for DPC-046 generated from best-fit line graphs (all $r^2$=0.99) were 13.4 M for TrkB, 15.4 M for IRAK-4, and 19.1 µM for PIM-1. At the highest DPC-046 concentration tested (50 µM), inhibition of the respective kinases was TrkB (98%), IRAK-4 (92%), and PIM-1 (84%).

Figure 6:
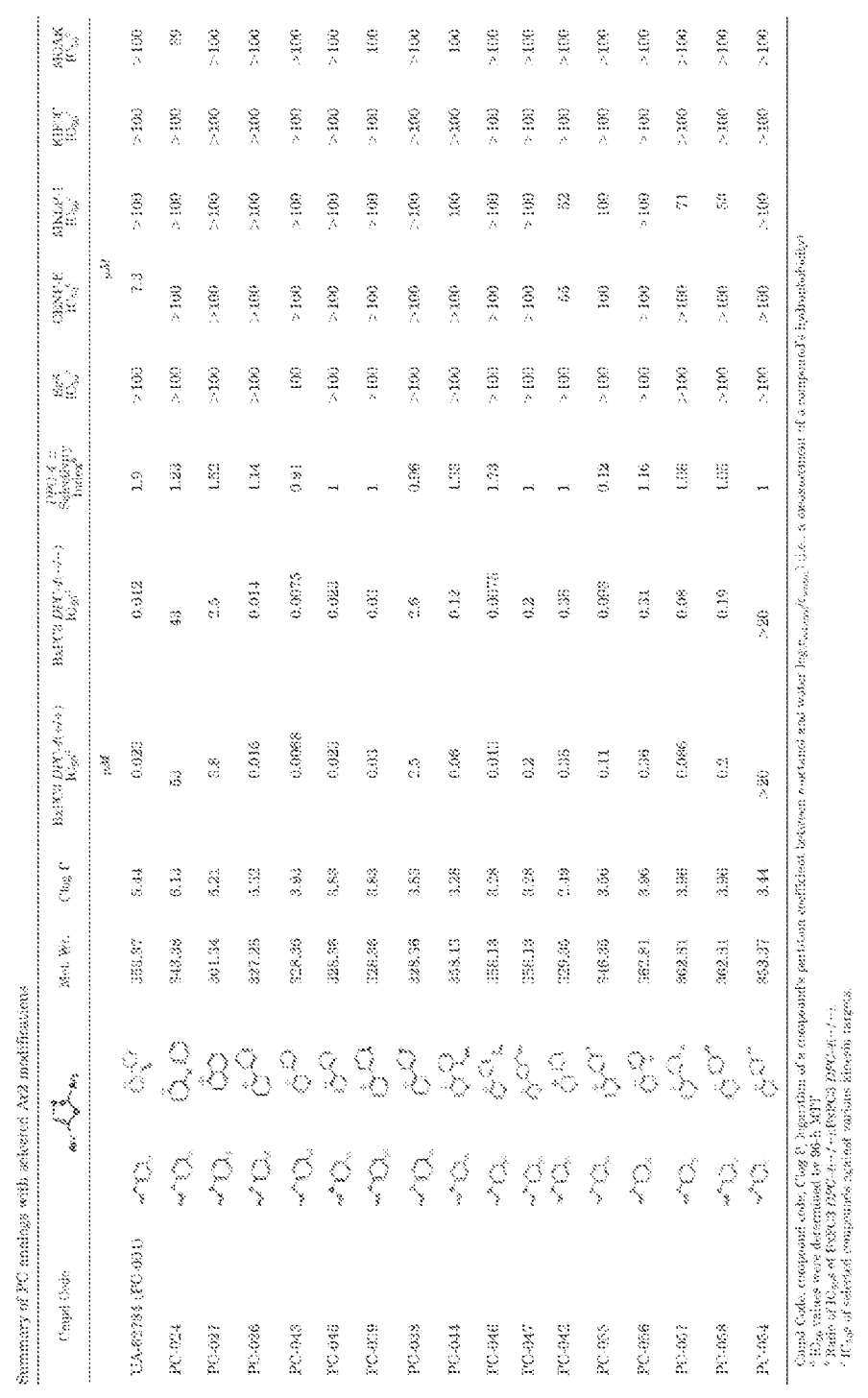
Figure 7:
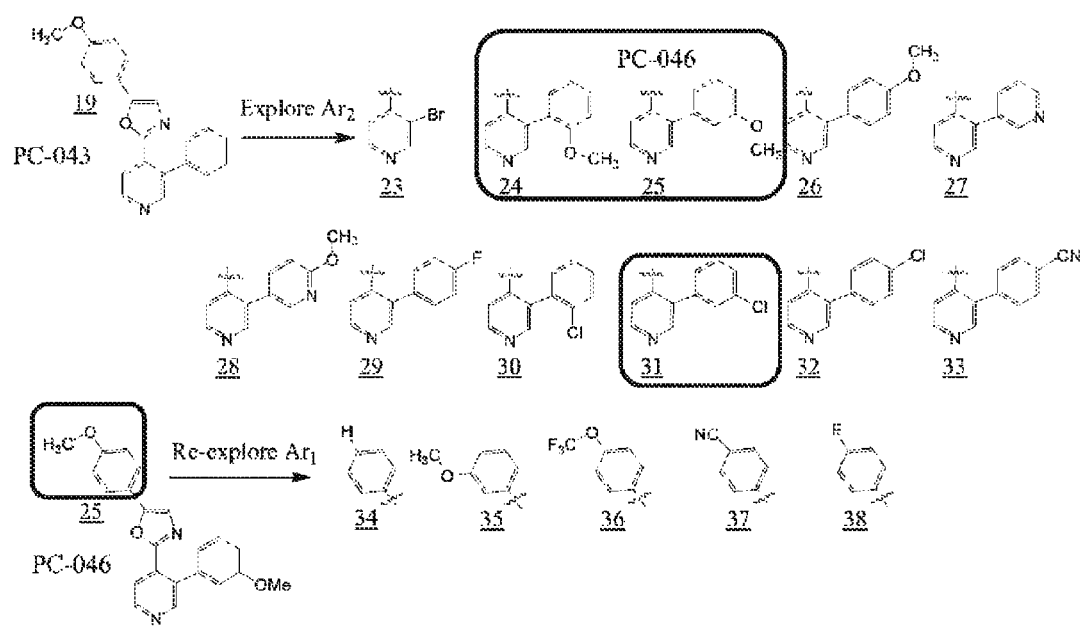
FIG. 7 depicts SAR exploration of the (D)PC-043 diaryl oxazole series.

Cell Cycle Arrest and Induction of Cell Death. Cell cycle analyses showed a reduction in the percentage of G0/G1-phase cells and a commensurate increase in G2/M-phase cells (FIG. 6) Annexin V/PI staining was used to distinguish the mechanism of cell death in BxPC3 cells treated with DPC-046 Annexin V-stained (singly) cells were identified as undergoing early apoptosis and dual Annexin V and PI stained cells to be undergoing necrosis. At the highest concentration used (1500 nM), cell death by a combination of apoptosis and necrosis was observed (FIG. 7).

Macromolecule Synthesis. There was no selective inhibition of synthesis of DNA, RNA, or protein by DPC-046, i.e., the inhibition of cell growth by DPC-046 was not preferentially due to the inhibition of DNA synthesis, RNA synthesis, or protein synthesis. These studies were performed at 24 to 72 h. The $IC_{50}$ for inhibition of synthesis of each macromolecule averaged approximately 3 µM at 72 h.

Pharmacokinetic Studies. The pharmacokinetics of DPC-046 was studied in mice that were given a single intravenous tail vein injection of 88 mg/kg PC-046. The mean (S.D.) peak plasma concentration of 10.8 (4.26)µM was obtained at the first sampling time (1 min). The drug was still detectable in the plasma at the last sampling time of 24 h, with a mean (S.D.) concentration of 0.226 (0.104) µM. A monoexponential half-life of 7.5 h was observed in mouse plasma, and the AUC was 5.9 h*g/ml. This relatively long half-life could be explained by a low clearance (14.9 l/h/kg) and a large apparent volume of distribution (135.2 l/kg). DPC-046 was 91% bound to plasma proteins in mouse plasma and 85% bound in human plasma at a plasma concentration of 3.27 µM. These results suggest extensive binding to tissues.

Stability Studies. LC-MS was used to evaluate the stability of DPC-046 kept at −20° C. or at 22° C., unprotected from light. After 2 years of storage, there was a measurable (8.6%) loss of parent compound when stored at −20° C. in the dark and a 43.6% loss at 22° C. in light.

Figure 8:
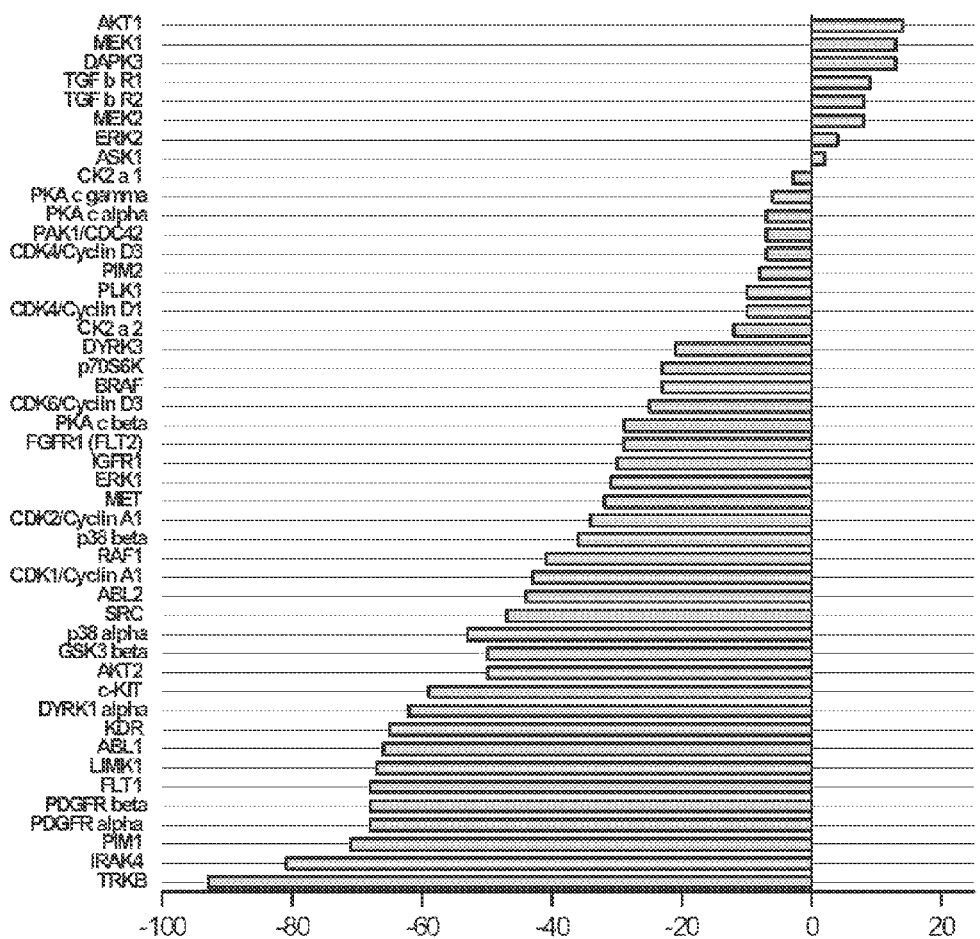
FIG. 8 depicts the results of a kinase profiling summary.

Antitumor Efficacy Studies. Studies of antitumor efficacy were performed in SCID mice with human MiaPaCa-2 cells in Matrigel implanted subcutaneously in the front flank. An initial dose-ranging study evaluated a 5 consecutive daily administration of 44 or 66 mg/kg/day PC-046. The 66 mg/kg/day dose was not tolerated (−15% weight loss, 60% death) so an intermediate dose of 55 mg/kg/day, daily for 5 days, was evaluated. This dose resulted in substantial (10%) weight loss but reduced MiaPaCa-2 tumor growth compared with untreated controls (preliminary data not shown). In another experiment comparing 44 or 55 mg/kg/day DPC-046 administered daily for 5 days, there was significant inhibition of MiaPaCa-2 tumor growth compared with the untreated group (FIG. 8). This was associated with a statistically significant reduction in the area under the tumor size X time curve compared with controls (p=0.014) (FIG. 9) in the 55 mg/kg/day PC-046-treated group. However, the lower 44 mg/kg/day dose was not effective. It is noteworthy that, although the mice in the 55 mg/kg/day group lost an average of 15.8% of their body weight while they were receiving DPC-046 injections, their body weight had recovered by the end of the study.

Figure 9:
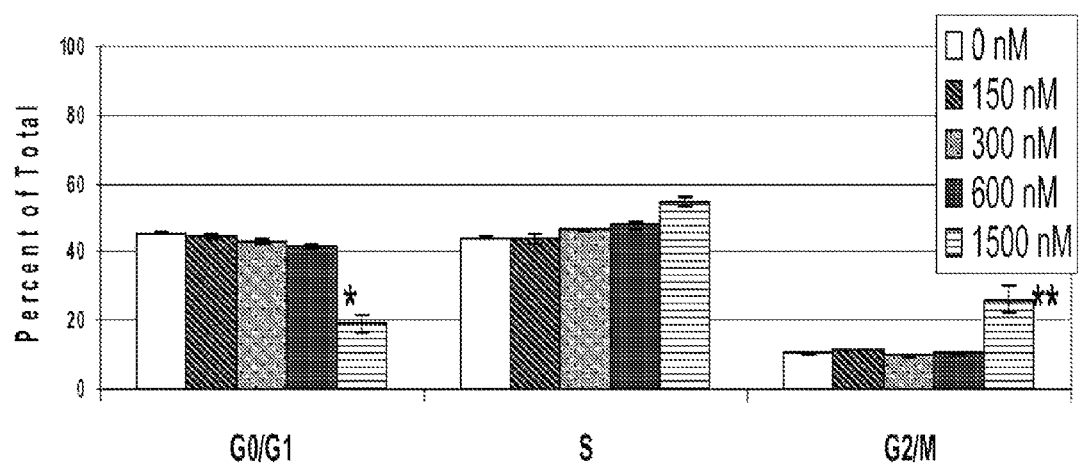
FIG. 9 depicts percentages of BxPC3 DPC-4(−/−) cells in the indicated cell cycle phases treated with increasing concentrations of (D)PC-046 for 24 hours.
Figure 10:
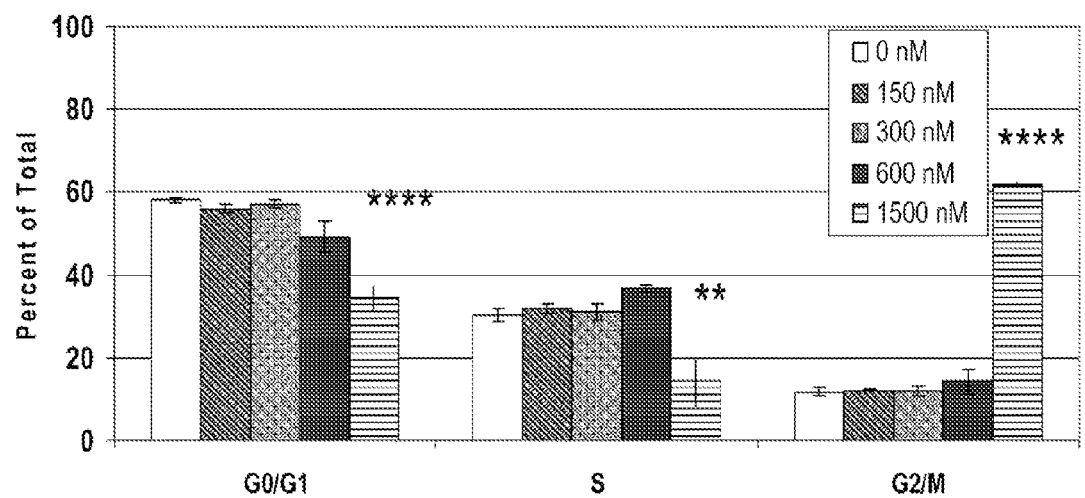
FIG. 10 depicts percentages of BxPC3 DPC-4(−/−) cells in the indicated cell cycle phases treated with increasing concentrations of (D)PC-046 for 48 hours.
Figure 11:
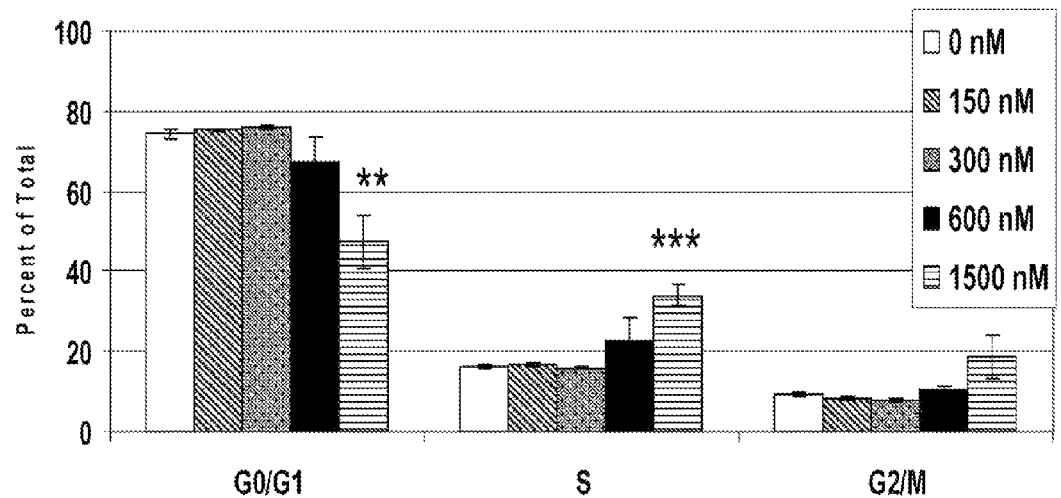
FIG. 11 depicts percentages of BxPC3 DPC-4(−/−) cells in the indicated cell cycle phases treated with increasing concentrations of (D)PC-046 for 72 hours (FIG. 11).
Figure 12:
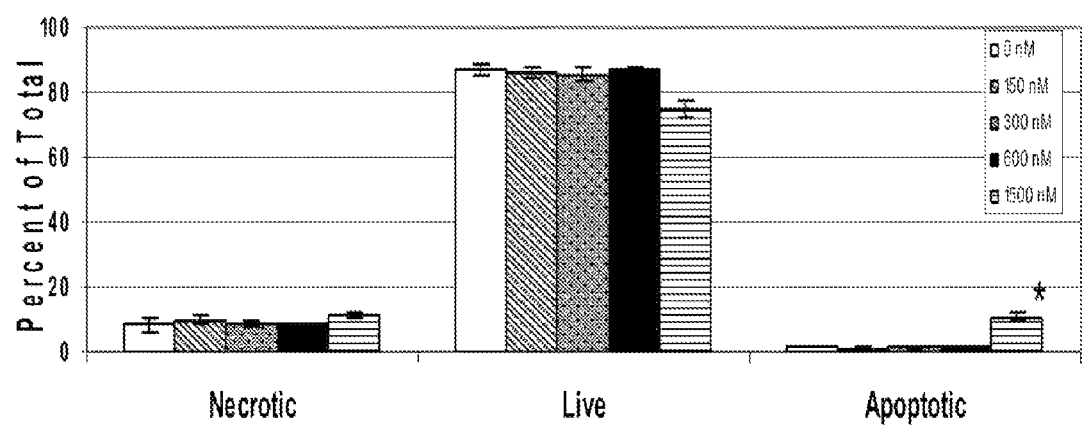
FIG. 12 depicts percentages of live, early apoptotic and necrotic in BxPC3 DPC-4(−/−) cells treated with increasing concentrations of (D)PC-046 for 24 hours.
Figure 13:
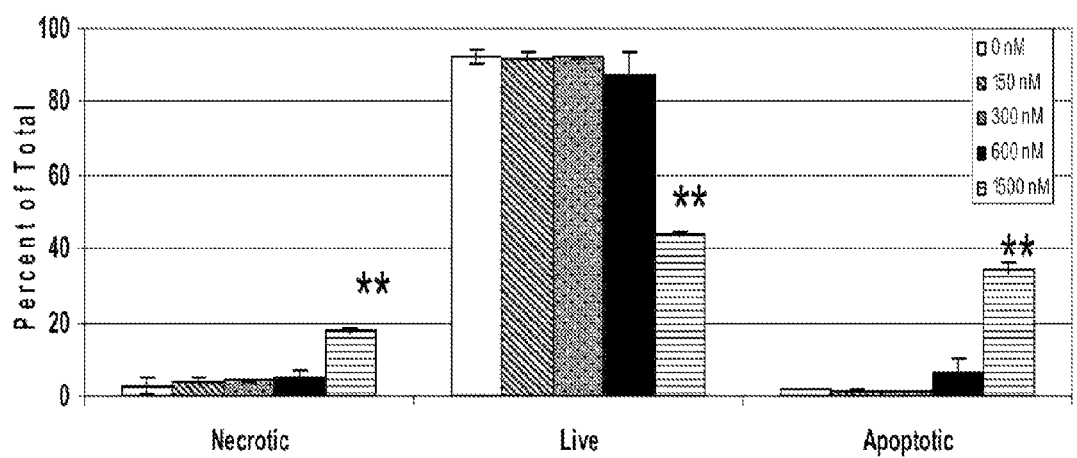
FIG. 13 depicts percentages of live, early apoptotic and necrotic in BxPC3 DPC-4(−/−) cells treated with increasing concentrations of (D)PC-046 for 48 hours.
Figure 14:
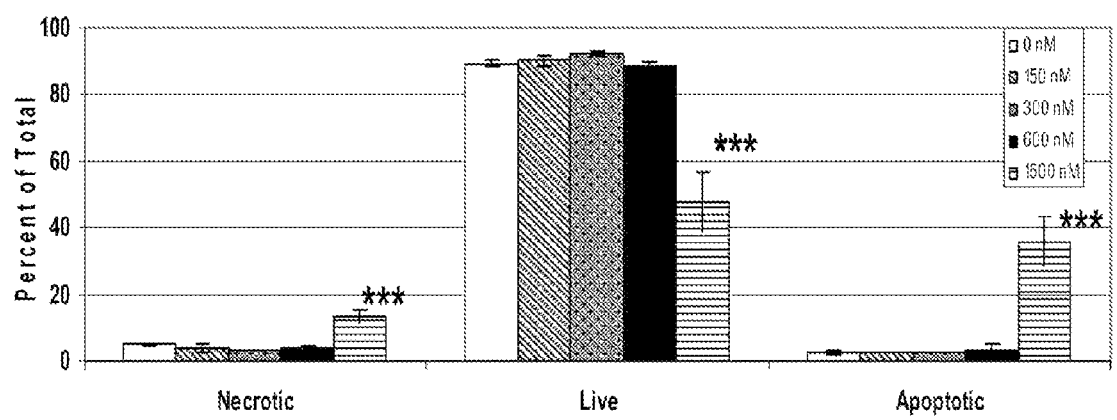
FIG. 14 depicts percentages of live, early apoptotic and necrotic in BxPC3 DPC-4(−/−) cells treated with increasing concentrations of (D)PC-046 for 72 hours.
Figure 15:
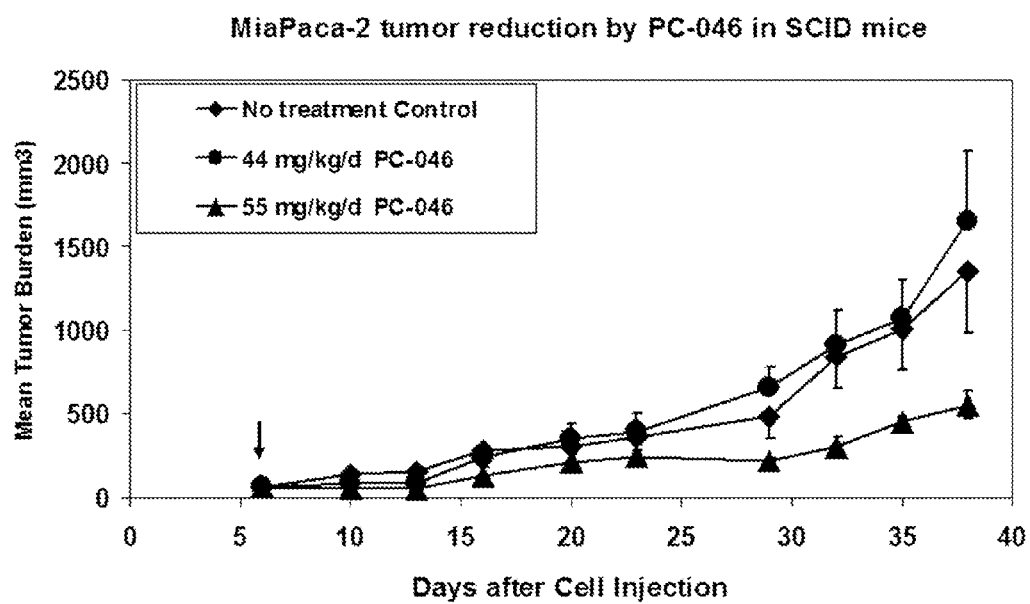
FIG. 15 depicts the mean tumor burden of SCID mice implanted subcutaneously with $10 \times 10^6$ MiaPaCa-2 cells in MatriGel then injected with vehicle alone or 44 or 55 mg/kg/day (D)PC-046 intraperitoneally daily for 5 consecutive days.
Figure 16:
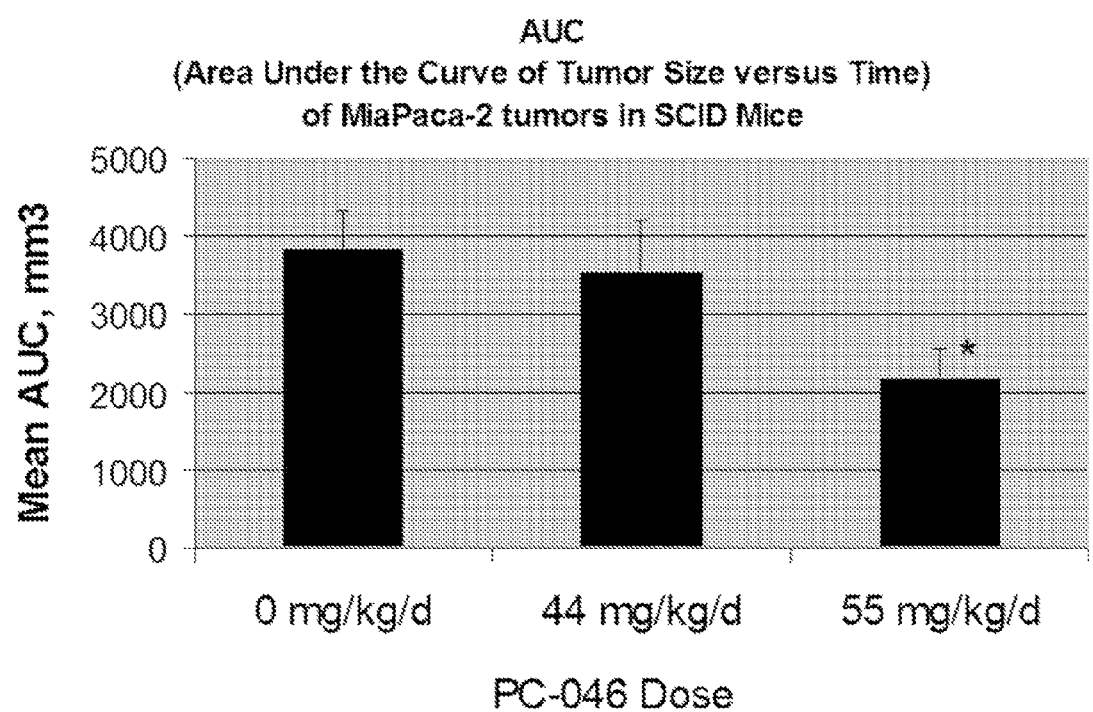
FIG. 16 depicts the AUC of tumor size versus time of MiaPaCa-2 tumors in SCID mice.

Referring now to FIGS. 1 and 2, synthetic approaches to diaryl oxazoles are depicted a, N-bromosuccinimide, trimethylsilyl trifluoromethanesulfonate. b, NaN3, DMSO, 30 min rt. c, PPh3, TsOH, tetrahydrofuran, 24 h. d, EDC, DIEA, DCM. e, POCl3/DMF (1:5), 80° C., 2 h. f, Ar—B(OH)2, Pd(PPh3)4, Na2CO3, DME/H2O (3:1), reflux, 2 h. FIG. 3 depicts the structures of (D)PC-033, (D)PC-032, and (D)PC-046. FIG. 4 depicts SAR exploration of the UA-62784 (D)PC-001 fluorenone series. FIG. 5 depicts a summary of (D)PC analogs with selected Ar1 modifications. Cmpd Code=compound code; Clog P=logarithm of a compound's partition coefficient between n-octanol and water $\log(c_{octanol}/c_{water})$ (i.e., a measurement of a compound's hydrophobicity). Values labeled with (a) are $IC_{50}$ values determined by 96-h MTT. Values labeled with (b) indicate a ratio of $IC_{50}$ values of BxPC3 DPC-4(+/+):BxPC3 DPC-4(−/−). Values labeled with (c) $IC_{50}$ values of the listed compounds against the indicated kinesin targets. FIG. 6 depicts a summary of (D)PC analogs with selected Ar2 modifications. Cmpd Code=compound code; Clog P, logarithm of a compound's partition coefficient between n-octanol and water $\log(c_{octanol}/c_{water})$ (i.e., a measurement of a compound's hydrophobicity). Values labeled with (a) are $IC_{50}$ values were determined by 96-h MTT. Values labeled with (b) are the ratio of $IC_{50}$ values of BxPC3 DPC-4(+/+):BxPC3 DPC-4(−/−). Values labeled with (c) are the $IC_{50}$ values of the listed compounds against the indicated kinesin targets. FIG. 7 depicts SAR exploration of the (D)PC-043 diaryl oxazole series. FIG. 8 depicts the results of a kinase profiling summary. Kinase screening was performed using 25 µM (D)PC-046 in a cell-free in vitro kinase activity assay by measuring [$^{33}$P]ATP incorporation into a specific kinase substrate. The x-axis shows the percentage of change in activity against the listed kinases (y-axis). FIGS. 9, 10, and 11 show that (D)PC-046 causes a block in the S and G2/M-phases in BxPC3 DPC-4 (−/−) cells. BxPC3 DPC-4(−/−) cells were treated with increasing concentrations of (D)PC-046 for 24 hours (FIG. 9), 48 hours (FIG. 10), or 72 hours (FIG. 11). Cell cycle was measured by PI staining and analyzed by flow cytometry. The percentage of cells in each indicated cell cycle phase are shown. Mean±S.E.M., n=3. Statistically different from untreated group at *, p<0.05; , p<0.01; *, p<0.005; ****, p<0.001. FIGS. 12, 13, and 14 show that (D)PC-046 causes both early apoptotic and necrotic cell death in BxPC3 DPC-4(−/−) cells. BxPC3 DPC-4(−/−) cells were treated with increasing concentrations of (D)PC-046 for 24 hours (FIG. 12), 48 hours, (FIG. 13), or 72 hours (FIG. 14) The percentage of necrotic, viable, and early apoptotic cells was measured by dual labeling using Annexin V-Alexa Fluor 488, and PI and analyzed by flow cytometry. Mean±S.E.M., n=3. Statistically different from untreated group at *, p<0.002; , p<0.001; *, p<0.01. FIG. 15 depicts the antitumor efficacy of (D)PC-046 in SCID mice. $10\times10^6$ MiaPaCa-2 cells in MatriGel were implanted subcutaneously into the flanks of SCID mice. Mice were randomized on day 6 (arrow) and then injected with vehicle alone or 44 or 55 mg/kg/day (D)PC-046 intraperitoneally daily for 5 consecutive days. Mean tumor burden is shown. Mean±S.D. (n=4 or 5). FIG. 16 depicts the AUC of tumor size versus time of MiaPaCa-2 tumors in SCID mice. The AUC of each individual mouse was calculated (days 6 to 23) and then averaged. Results are mean±S.E.M. Statistically different from no treatment group at *, p=0.014.

$IC_{50}$ values of the indicated examples in the indicated tumor cell lines are shown in Table 1.

TABLE 1

| | Tumor type | | | |
| | Prostate | | Lung | |
| Cell line | PC3 | DU145 | H460 | A549 |
| --- | --- | --- | --- | --- |
| DPC042 | $1.1 \times 10^{-6}$ | $1.3 \times 10^{-6}$ | $1.3 \times 10^{-8}$ | $1.1 \times 10^{-8}$ |
| DPC043 | $9.9 \times 10^{-9}$ | $2.0 \times 10^{-8}$ | $5.0 \times 10^{-8}$ | $3.3 \times 10^{-8}$ |
| DPC044 | $2.4 \times 10^{-8}$ | $3.4 \times 10^{-8}$ | $4.9 \times 10^{-8}$ | $4.0 \times 10^{-8}$ |
| DPC046 | $6.5 \times 10^{-9}$ | $2.7 \times 10^{-8}$ | $2.5 \times 10^{-8}$ | $2.2 \times 10^{-8}$ |
| DPC047 | $3.8 \times 10^{-7}$ | $5.0 \times 10^{-7}$ | $9.4 \times 10^{-9}$ | $6.2 \times 10^{-9}$ |
| DPC049 | $1.2 \times 10^{-5}$ | $8.7 \times 10^{-6}$ | $>2 \times 10^{-5}$ | $>2 \times 10^{-5}$ |
| DPC050 | $>2 \times 10^{-5}$ | $>2 \times 10^{-5}$ | $>2 \times 10^{-5}$ | $>2 \times 10^{-5}$ |
| DPC051 | $1.3 \times 10^{-5}$ | $>2 \times 10^{-5}$ | $1.2 \times 10^{-5}$ | $>2 \times 10^{-5}$ |
| DPC052 | $1.4 \times 10^{-5}$ | $1.8 \times 10^{-5}$ | $>2 \times 10^{-5}$ | $>2 \times 10^{-5}$ |
| DPC053 | $7.1 \times 10^{-6}$ | $7.1 \times 10^{-6}$ | $8.1 \times 10^{-6}$ | $5.3 \times 10^{-6}$ |
| DPC054 | $>2 \times 10^{-5}$ | $>2 \times 10^{-5}$ | $>2 \times 10^{-5}$ | $>2 \times 10^{-5}$ |
| DPC055 | $1.3 \times 10^{-7}$ | $2.0 \times 10^{-7}$ | $2.3 \times 10^{-7}$ | $2.3 \times 10^{-7}$ |
| DPC056 | $3.6 \times 10^{-7}$ | $3.7 \times 10^{-7}$ | $5.0 \times 10^{-7}$ | $6.4 \times 10^{-7}$ |
| DPC057 | $2.8 \times 10^{-8}$ | $4.6 \times 10^{-8}$ | $6.1 \times 10^{-8}$ | $5.8 \times 10^{-8}$ |
| DPC058 | $1.6 \times 10^{-7}$ | $2.4 \times 10^{-7}$ | $1.9 \times 10^{-7}$ | $3.4 \times 10^{-7}$ |

IC50 values of (D)PC-044 and (D)PC-046 were also determined for the indicated tumor cell lines in Table 2.

TABLE 2

| | Tumor type | | | | | | | | | |
| | Ovarian | | Kidney | | Breast | | Prostate | | Lung | |
| Cell Line | OVCAR3 | SK-OV-3 | A498 | Caki-1 | MCF7 | MDA231 | PC3 | DU145 | H460 | A549 |
| --- | --- | --- | --- | --- | --- | --- | --- | --- | --- | --- |
| DPC044 | $1.6 \times 10^{-8}$ | $2.3 \times 10^{-8}$ | $2.0 \times 10^{-8}$ | $2.0 \times 10^{-8}$ | $1.6 \times 10^{-8}$ | $3.0 \times 10^{-8}$ | $2.4 \times 10^{-8}$ | $3.4 \times 10^{-8}$ | $4.9 \times 10^{-8}$ | $4.0 \times 10^{-8}$ |
| DPC046 | $1.3 \times 10^{-8}$ | $1.7 \times 10^{-8}$ | $1.4 \times 10^{-8}$ | $1.3 \times 10^{-8}$ | $1.1 \times 10^{-8}$ | $1.7 \times 10^{-8}$ | $6.5 \times 10^{-9}$ | $2.7 \times 10^{-9}$ | $2.5 \times 10^{-8}$ | $2.2 \times 10^{-8}$ |

REFERENCES

So as to reduce the complexity and length of the Detailed Specification, and to fully establish the state of the art in certain areas of technology, Inventors herein expressly incorporate by reference to the extent allowed all of the following materials in their entirety.

Boxenbaum H and Ronfeld R, *Am J Physiol* 245, R768-R775 (1983).
Burris H 3rd and Rocha-Lima C *Oncologist* 13, 289-298 (2008).
Collins P J et al, *J Forensic Sci* 49, 1265-1277 (2004).
Darzynkiewicz Z et al, *Cytometry* 25, 1-13 (1996).
Desmet C J and Peeper D S, *Cell Mol Life Sci* 63, 755-759 (2006).
Funk C J et al, *Anal Biochem* 329, 68-76 (2004).
Geiger T R and Peeper D S, *Cancer Res* 67, 6221-6229 (2007).
Guha S K et al, *Tetrahedron Lett* 47, 291-293 (2006).
Henderson M C et al, *Mol Cancer Ther* 8, 36-44 (2009).
Hirokawa N and Noda Y, *Physiol Rev* 88, 1089-1118 (2008).
Holub J M et al, *Molecules* 9, 134-157 (2004).
Huang Y S et al, *Cell Mol Immunol* 2, 36-39 (2005).
Hunter A W et al, *Mol Cell* 11, 445-457 (2003).
Jaffee E M et al, *Cancer Cell* 2, 25-28 (2002).
Jemal A et al, *CA Cancer J Clin* 58, 71-96 (2008).
Jones S et al, *Science* 321, 1801-1806 (2008).
Li Y Y et al, *Cancer Res* 66, 6741-6747 (2006).
Lieber M et al, *Int J Cancer* 15, 741-747 (1975).
Lombillo V A et al, *J Cell Biol* 128, 107-115 (1995).
Meanwell N A et al, *J Med Chem* 36, 3884-3903 (1993).
Miyaki M and Kuroki T, *Biochem Biophys Res Commun* 306, 799-804 (2003).
Mosmann T, *J Immunol Methods* 65, 55-63 (1983).
Nicolaou K C et al, *J Am Chem Soc* 126, 12897-12906 (2004).
Nislow C, et al, *Nature* 359, 543-547 (1992).
Sawin K E et al, *Nature* 359, 540-543 (1992).
Sclabas G M et al, *Clin Cancer Res* 11, 440-449 (2005).
Tan M H et al, *Cancer Invest* 4, 15-23 (1986)
Tascilar M et al, *Clin Cancer Res* 7, 4115-4121 (2001).
Vermes I et al, *J Immunol Methods* 184, 39-51 (1995).
Wang H et al, *Cancer Res* 66, 9722-9730 (2006).
Yang Z and Goldstein L S, *Mol Biol Cell* 9, 249-261. (1998)
Yen T J et al, *EMBO J* 10, 1245-1254 (1991).
Yunis A A et al, *Int J Cancer* 19, 128-135 (1977).

We claim:

1. A compound with the formula;

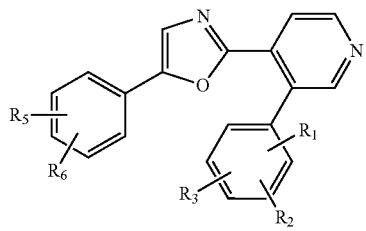

wherein $R_5$ is selected from the group consisting of H, alkyl, OH, OR', SH, $S(O)_nR'$, halogen, CN, $CO_2H$, $CO_2R'$, CONHR', $SO_2NHR'$, $CF_3$, $OCF_3$, and $O(CH_2)_nO$ wherein R' is selected from the group consisting of H and lower alkyl and wherein n is an integer;

wherein $R_6$ is selected from the group consisting of H, alkyl, OH, OR', SH, $S(O)_nR'$, halogen, CN, $CO_2H$, $CO_2R'$, CONHR', $SO_2NHR'$, $CF_3$, $OCF_3$, and $O(CH_2)_nO$ wherein R' is selected from the group consisting of H and lower alkyl and wherein n is an integer;

wherein $R_1$ is selected from the group consisting of H, alkyl, OH, OR', SH, $S(O)_nR'$, halogen, ON, $CO_2H$, $CO_2R'$, CONHR', $SO_2NHR'$, $CF_3$, $OCF_3$, and $O(CH_2)_nO$ wherein R' is selected from the group consisting of H and lower alkyl and wherein n is an integer;

wherein $R_2$ is selected from the group consisting of H, alkyl, OH, OR', SH, $S(O)_nR'$, halogen, CN, $CO_2H$, $CO_2R'$, CONHR', $SO_2NHR'$, $CF_3$, $OCF_3$, and $O(CH_2)_nO$ wherein R' is selected from the group consisting of H and lower alkyl and wherein n is an integer; and wherein $R_3$ is selected from the group consisting of H, alkyl, OH, OR', SH, $S(O)_nR'$, halogen, ON, $CO_2H$, $CO_2R'$, CONHR', $SO_2NHR'$, $CF_3$, $OCF_3$, and $O(CH_2)_nO$ wherein R' is selected from the group consisting of H and lower alkyl and wherein n is an integer.

2. The compound of claim 1 further comprising a pharmaceutically acceptable salt thereof.

3. A method of slowing the expansion of a pancreatic cancer cell comprising:
administering an effective amount of a pharmaceutical composition comprising the compound of claim 1 or pharmaceutically acceptable salts thereof to the pancreatic cancer cell.

4. The method of claim 3 wherein the pharmaceutical composition further comprises a pharmaceutically acceptable carrier.

5. The method of claim 3 wherein the compound is

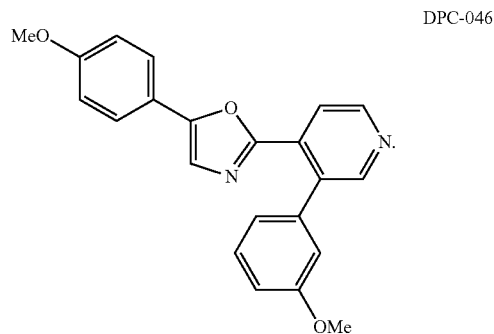 [SMILES: COc1ccc(-c2cnc(-c3ccncc3-c3cccc(OC)c3)o2)cc1]

6. A method of treating cancer comprising:
administering to a mammal having cancer an effective amount of a first pharmaceutical composition comprising an effective amount of a pharmaceutical composition comprising the compound of claim 1 or pharmaceutically acceptable salts thereof.

7. The method of claim 6 wherein the first pharmaceutical composition further comprises a pharmaceutically acceptable carrier.

8. The method of claim 6 wherein the mammal is a human.
9. The method of claim 6 wherein the compound is
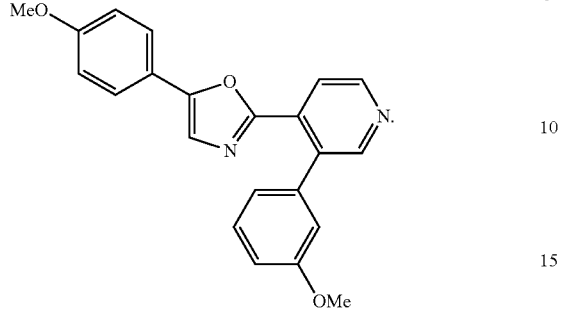
DPC-046
10. The method of claim 6 wherein the cancer is selected from the group consisting of: pancreatic cancer, ovarian cancer, breast cancer, colon cancer, myeloma, leukemia, kidney cancer, and lung cancer.
11. The method of claim 6 wherein the cancer is metastatic.
* * * * *